United States Patent [19]

Martel et al.

[11] Patent Number: 4,639,335
[45] Date of Patent: Jan. 27, 1987

[54] STEREOCONTROLLED ACETOXYAZETIDINONE PROCESS

[75] Inventors: Alain Martel, Delson; Jean-Paul Daris, St-Hubert, both of Canada

[73] Assignee: Bristol-Myers Company, New York, N.Y.

[21] Appl. No.: 818,145

[22] Filed: Jan. 13, 1986

Related U.S. Application Data

[62] Division of Ser. No. 597,765, Apr. 6, 1984.

[51] Int. Cl.[4] .................. C07D 499/00; A61K 31/425
[52] U.S. Cl. ..................................... 540/304; 540/357
[58] Field of Search ................ 260/245.2 R, 245.2 T; 514/210

[56] References Cited

U.S. PATENT DOCUMENTS 4,468,351 8/1984 Pirie et al. .................... 260/245.2 R

FOREIGN PATENT DOCUMENTS 2045755 11/1980 United Kingdom .

OTHER PUBLICATIONS

Heterocycles 17: 201–207 (1982) Hirai et al., J. Org. Chem. 42: 2960–2965 (1977) DiNinno et al.
Tetrahedron Letters 23(39): 4021–4024 (1982) Hirai et al.
Tetrahedron Letters 23(22): 2293–2296 (1982) Reider et al.
Chem. Pharm. Bull 29(11): 3158–3172 (1981) Hayashi et al.

Primary Examiner—Nicholas S. Rizzo
Attorney, Agent, or Firm—David M. Morse

[57] ABSTRACT

A novel stereocontrolled process is disclosed for converting 6-aminopenicillanic acid to an optically active azetidinone of the formula

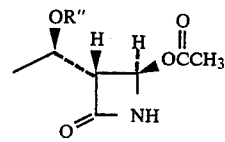

wherein R" is a hydroxy-protecting group by use of a 6,6-dihaloanhydropenicillin or 6,6-bis(phenylselenyl)anhydropenicillin intermediate.

11 Claims, No Drawings

STEREOCONTROLLED ACETOXYAZETIDINONE PROCESS

CROSS-REFERENCE TO RELATED APPLICATION

This application is a division of co-pending application Ser. No. 597,765 filed Apr. 6, 1984.

BACKGROUND OF THE INVENTION

1. Field of the Invention

The present invention is directed to a novel stereocontrolled process for producing a key intermediate used in the synthesis of carbapenem and penem antibiotics.

2. Description of the Prior Art

The present invention is directed to a novel stereocontrolled process for converting 6-aminopenicillanic acid to an optically active azetidinone intermediate of the formula

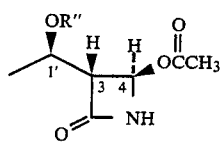

wherein R" is a conventional hydroxy-protecting group and wherein the absolute configuration at carbons 1', 3 and 4 is R, R and R. Intermediates of formula I, which are known per se, are key intermediates in the synthesis of carbapenem and penem antibiotics having an (R)-hydroxyethyl substituent at the 6-position of the carbapenem or penem nucleus and the absolute configuration R and S at the 5 and 6 positions, respectively. A wide variety of such compounds, including the natural fermentation product thienamycin, have been reported in the patent and scientific literature as having exceptional antibacterial activity.

Several total synthesis procedures have been reported for preparation of the above-described penem and carbapenem antibiotics, but to date such procedures have been unsatisfactory from a commercial standpoint due to the large number of steps required and the necessity of separating diastereomer mixtures formed in such procedures.

One approach to synthesis of carbapenems and penems of the above-described type has been to use as a starting material, 6-aminopenicillanic acid (6-APA), a readily-available substance easily obtained by fermentation procedures. Hirai, et al. in *Heterocycles* 17: 201–207 (1982) report a process for converting 6-APA to the optically active 4-acetoxy-3-azetidinone of the formula

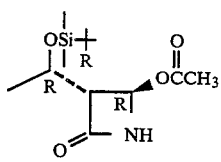

which can be converted, by known procedures, to biologically active penems and carbapenems. In this process 6-APA is converted to the above-indicated azetidinone by the following scheme:

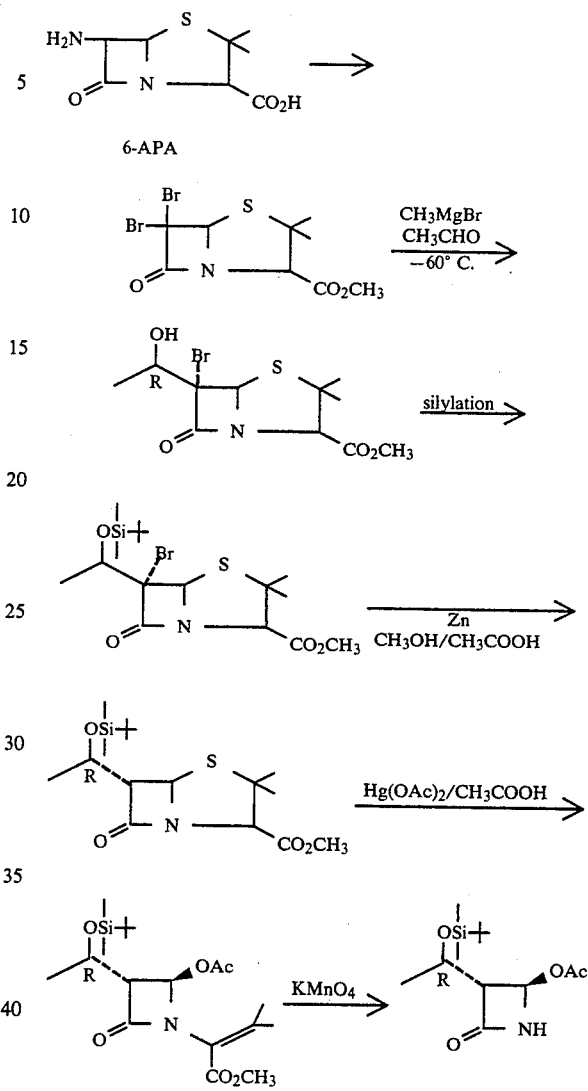

To elaborate, 6-APA is esterified to give the methyl ester and then converted by known methods, e.g. those described in U.K. 2,045,755A, to give the methyl ester of 6,6-dibromopenicillin. This ester is then hydroxyethylated by the metal-halogen exchange process described in *J. Org. Chem.* 42: 2960–2965 (1977) to give a mixture of cis and trans diastereomers which, at least on a small scale, can be chromatographically separated to yield the desired (R)-hydroxyethyl cis-isomer. This isomer is silylated with t-butyldimethylchlorosilane to give the corresponding hydroxy-protected intermediate which is then subjected to reductive debromination with Zn to give a mixture of the cis and trans (R)-hydroxyethyl products from which the desired trans isomer can be separated. The hydroxyethylated penicillin ester is then treated with $Hg(OAc)_2$ in acetic acid to cleave the thiazolidine ring and form a 4-acetoxyazetidinone intermediate which is oxidized with $KMnO_4$ to remove the β-methylcrotonate moiety and form the desired optically active 4-acetoxyazetidinone intermediate.

*Tetrahedron Letters* 23(39): 4021–4024 (1982) describes the following reaction scheme:

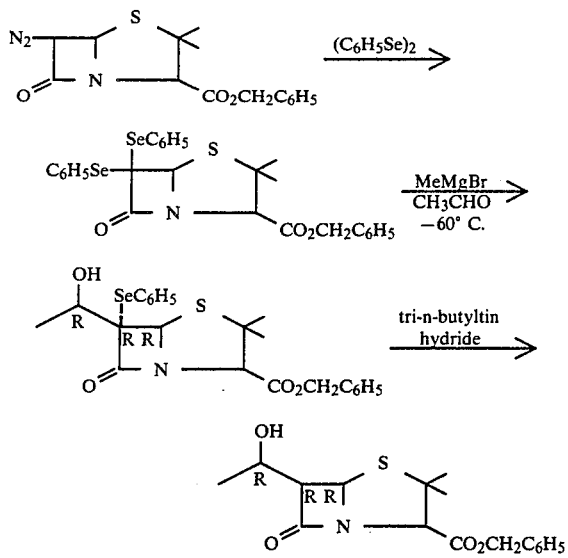

Thus, the diazopenicillin ester starting material was converted into benzyl 6,6-bis(phenylselenyl)penicillinate which was hydroxyethylated with MeMgBr and CH₃CHO at −60° C. to give a mixture of diastereomers from which the desired cis isomer can be isolated.

The optically active 4-acetoxyazetidinone can be used in known procedures in the synthesis of carbapenem and penem antibiotics. For example, *Tetrahedron Letters* 23(22): 2293-2296 (1982) describes conversion of this intermediate to thienamycin and *Chem. Pharm. Bull.* 29(11): 3158-3172 (1981) describes use of this intermediate to prepare penem antibiotics.

While the above-described procedures are potentially useful for large scale synthesis of (8R)-hydroxyethyl penem and carbapenem antibiotics, they suffer from a lack of stereo-specificity in the aldol condensation step and in the reduction step, i.e. hydroxyethylation of the dibromopenicillin or bis(phenylselenyl)penicillin ester and reduction of such hydroxy-ethylated intermediates to remove the bromo or phenylseleno group gives a mixture of diastereomers which must be separated to give the desired optically active product. Such a separation, particularly on a commercial scale, results in the procedures being much less efficient then they might otherwise be.

SUMMARY OF THE INVENTION

The present invention provides a novel stereocontrolled process for converting 6-aminopenicillanic acid to the known optically active azetidinone intermediate of the formula

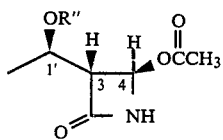

wherein R″ is a conventional hydroxy-protecting group and wherein the absolute configuration at carbons 1′, 3 and 4 is R, R and R. Such intermediates are key intermediates in the synthesis of a wide variety of previously disclosed carbapenem and penem antibiotics having an (R)-hydroxyethyl substituent at the 6-position of the carbapenem or penem nucleus and the absolute configuration R and S (trans) at the 5 and 6 positions, respectively. Also provided are certain novel intermediates used in such process.

More specifically the present invention provides an improved process for preparing the optically active azetidinone intermediate I which involves the steps of
(a) converting by per se known procedures 6-aminopenicillanic acid to an anhydropenicillin of the formula

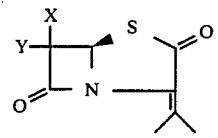

wherein X and Y are each independently chloro, bromo, iodo or phenylseleno (SeC₆H₅);

(b) reacting intermediate V with a reagent selected from a Grignard reagent of the formula R₁MgX or an organolithium compound of the formula R₁Li in which R₁ is (lower)alkyl or aryl and X is as defined above in an anhydrous inert organic solvent and at a temperature in the range of about 0° to −78° C. and subsequently adding acetaldehyde to produce exclusively the intermediate of the formula

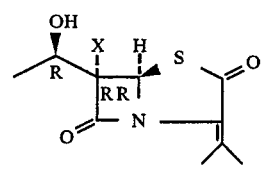

wherein X is as defined above;

(c) converting intermediate IIa to the corresponding intermediate of the formula

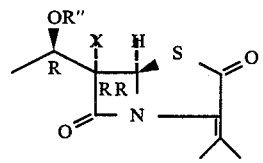

wherein R″ is a conventional hydroxy-protecting group, most preferably a bulky triorganosilyl group such as t-butyldimethylsilyl, t-butyldiphenylsilyl or triisopropylsilyl, and X is as defined above;

(d) subjecting intermediate IIb to reduction in an inert solvent and isolating the so-produced 5,6-trans isomer of the formula

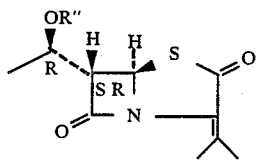

wherein R″ is as defined above;
(e) cleaving the thiazolidine ring of intermediate IIIb to produce an acetoxyazetidinone intermediate of the formula

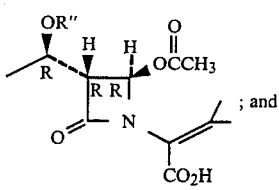

; and (f) oxidizing intermediate IV to remove the β-methylcrotonate moiety and produce the desired optically active intermediate I. In a variant of the above-described process, intermediate IIa may be reduced prior to protection of the hydroxy functional group.

Intermediates of the formulae

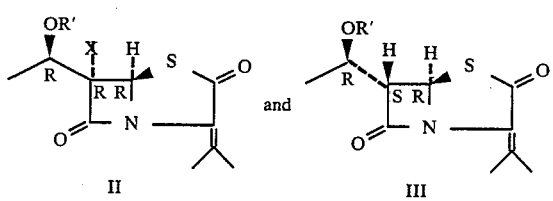

wherein X is chloro, bromo, iodo or phenylseleno and R' is hydrogen or a conventional hydroxy-protecting group are novel compounds and are included within the scope of the present invention.

DETAILED DESCRIPTION

The present invention provides a significant improvement in the prior art method of converting 6-aminopenicillanic acid to the key optically active acetoxyazetidinone intermediate I which is used to synthesize various carbapenem and penem antibiotics including the broad-spectrum carbapenem, thienamycin, of the formula

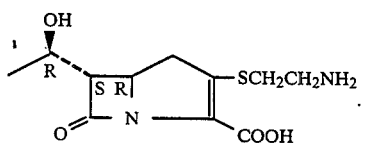

As noted above, prior art procedures for preparing (8R)-hydroxyethyl carbapenem and penem compounds via the 6-APA route involve an aldol condensation reaction to introduce the desired 6-hydroxyethyl substituent. One literature procedure involves converting 6-APA to the 6-acetyl derivative and then reducing this derivative to give the hydroxyethyl penicillin product (*JACS* 103: 6765-6767, 1981). The reduction step, however, is not stereospecific and the desired optical isomer must be separated from a mixture of diastereomers. Direct hydroxyethylation of a 6-halopenicillin, 6,6-dihalopenicillin or 6,6-bis(phenylselenyl)penicillin is disclosed, for example, in *Chem. Pharm. Bull.* 29(10): 2899-2909 (1981), *J. Org. Chem.* 42: 2960-2965 (1977), *Heterocycles* 17: 201-207 (1982) and *Tetrahedron Letters* 23(39): 4021-4024 (1982), but this procedure suffers from the fact that the aldol reaction on the penicillin intermediate is not stereospecific and it is necessary to separate out the desired (8R)-hydroxyethyl isomer before proceeding with the remaining steps of the synthesis.

The present invention is based on the unexpected discovery that an aldol condensation reaction on certain 6,6-disubstituted anhydropenicillins results in exclusive formation of only one stereoisomer, i.e. the isomer of the formula

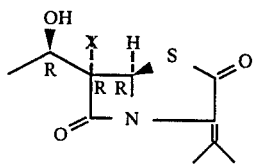

X = halo or phenylseleno which has the desired 5R, 6R, 8R stereochemistry. This stereo-specific hydroxyethylation eliminates the necessity of separating stereoisomers following this step and, coupled with the stereoselective reductive removal of X under the preferred conditions of the present invention, greatly improves the usefulness of the 6-APA route for synthesis of penem and carbapenem antibiotics.

The general reaction scheme for the present process is illustrated below for the case in which a 6,6-dibromopenicillin starting material is used:

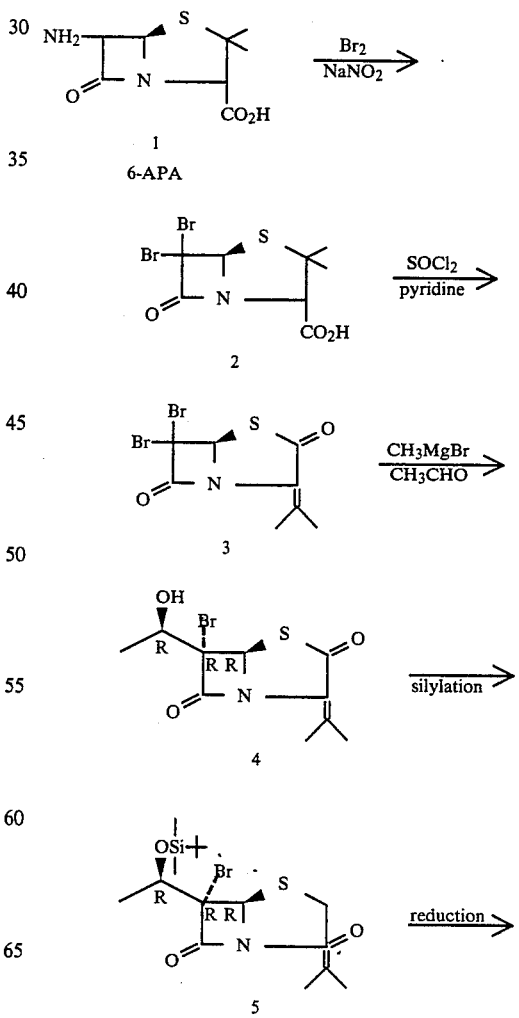

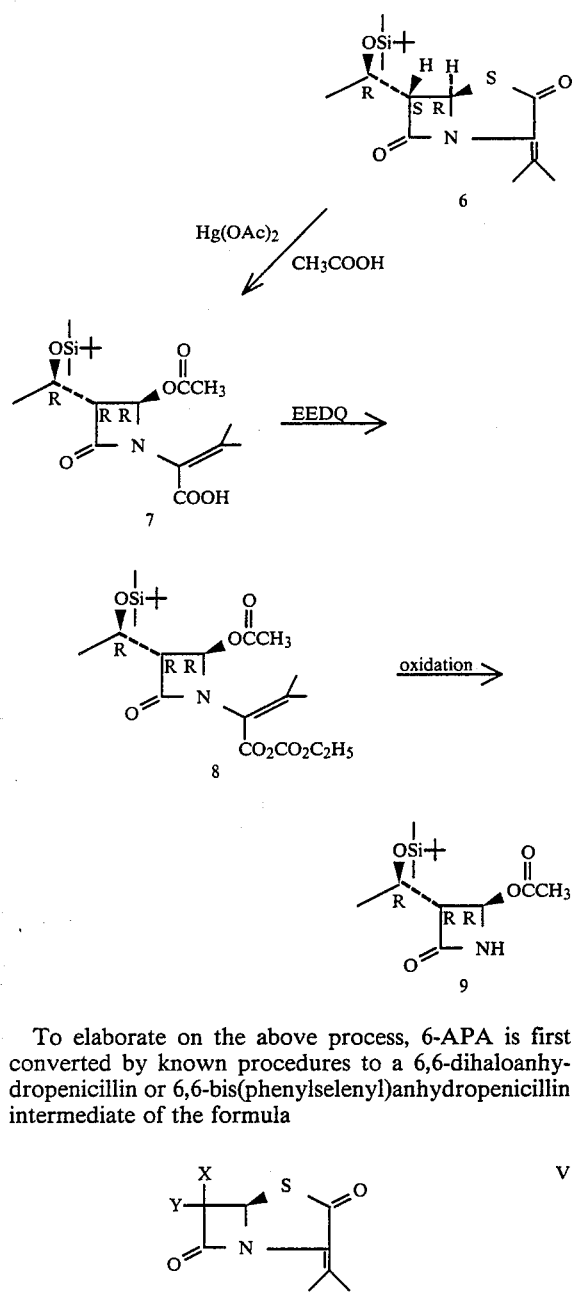

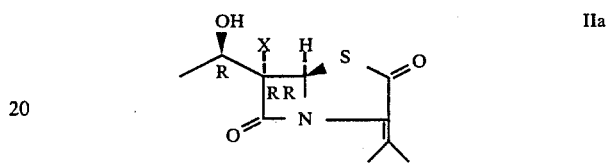

To elaborate on the above process, 6-APA is first converted by known procedures to a 6,6-dihaloanhydropenicillin or 6,6-bis(phenylselenyl)anhydropenicillin intermediate of the formula $$\text{V}$$

wherein X and Y are each independently chloro, bromo, iodo or phenylseleno. Intermediates of formula V, the starting materials for the novel reaction steps of the present invention, are known compounds or are prepared by known methods. These intermediates may be prepared by converting 6-APA to the corresponding 6,6-dihalopenicillanic acid or 6,6-bis(phenylselenyl)-penicillanic acid, forming an acid halide or mixed anhydride thereof and then reacting such acid halide or anhydride with a tertiary amine to give the anhydropenicillin. U.K. Pat. No. 2,405,755A discloses preparation of various 6,6-dihalopenicillanic acids such as 6,6-dibromopenicillanic acid, 6-chloro-6-iodopenicillanic acid, 6-bromo-6-iodopenicillanic acid and 6,6-diiodopenicillanic acid. Tetrahedron Letters 23(39): 4021–4024 (1982) discloses preparation of 6,6-bis(-phenylselenyl)penicillins. Conversion of 6,6-dihalopenicillanic acids to the corresponding anhydropenicillin is taught, for example, in J. Chem. Soc. (C): 2123–2127, 1969 where preparation of 6,6-dibromoanhydropenicillin is specifically disclosed. U.S. Pat. No. 3,311,638 teaches general procedures for converting penicillins to anhydropenicillins. The most preferred anhydropenicillin starting materials for use in the process of the present invention are 6,6-dihaloanhydropenicillins preferably 6,6-dibromoanhydropenicillin and 6-bromo-6-iodoanhydropenicillin, and most preferably 6,6-dibromoanhydropenicillin.

The anhydropenicillin starting material is subjected to an aldol condensation reaction to provide the desired hydroxy-ethylated intermediate of the formula IIa wherein X is chloro, bromo, iodo or phenylseleno, most preferably bromo, and wherein the absolute configuration is 5R, 6R, 8R. This is the key step in the present process as the aldol condensation on the anhydropenicillin intermediate results in exclusive formation of the desired optically active isomer, i.e. the stereoisomer having a cis-configuration at carbons 5 and 6 and an (8R)-hydroxyethyl substituent at position 6. This unexpected stereospecific aldol condensation eliminates the need for separation of diastereomers as required in prior art procedures and, therefore, greatly increases the practical utility of the 6-APA route for synthesis of carbapenem and penem end-products.

The aldol condensation may be carried out in essentially the same manner as in prior art reactions with penicillins, e.g. see J. Org. Chem. 42(18): 2960–2965, (1977). An enolate is first generated from the 6,6-dihaloanhydropenicillin by a metal-halogen exchange process at temperatures below about 0° C., e.g. 0° to −78° C., using an organolithium reagent or a Grignard reagent and the so produced enolate then reacted in situ with excess acetaldehyde to form the hydroxylated product.

The aldol reaction step is carried out in an inert anhydrous organic solvent, e.g. methylene chloride, chloroform, tetrahydrofuran, diethyl ether, toluene, dioxane, dimethoxyethane or mixtures thereof, at temperatures below 0° C. and preferably below about −20° C. The enolate is generated by use of about a molar equivalent of organolithium reagent or Grignard reagent.

Preferred organolithium reagents are those of the type $R_1Li$ in which $R_1$ is (lower)alkyl, i.e. $C_1$–$C_6$ alkyl, or aryl, i.e. $C_6$–$C_{10}$ aryl as phenyl. An example of a suitable organolithium reagent is n-butyllithium. The Grignard reagent is preferably a reagent of the type $R_1MgX$ where $R_1$ is $C_1$–$C_6$ alkyl or $C_6$–$C_{10}$ aryl and X is chloro, bromo or iodo. Preferred Grignard reagents are $CH_3MgBr$ and $CH_3MgCl$. A preferred embodiment comprises use of $CH_3MgCl$ at a temperature of about −40° C. to −45° C. Another preferred embodiment comprises use of $CH_3MgBr$ at a temperature of about −20° C. After formation of the enolate a molar excess of acetaldehyde is added to form the desired hydroxyethylated isomer.

Intermediate IIa may next be subjected to reduction to form the intermediate

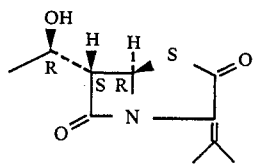 IIIa or, alternatively and preferably, intermediate IIa may first be converted to the corresponding anhydropenicillin intermediate in which the hydroxyl group is protected by a conventional hydroxy-protecting group and then reduced to form the hydroxyl-protected intermediate

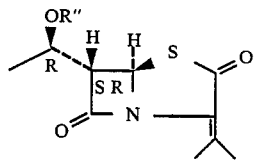 IIIb where R" is a conventional hydroxy-protecting group. If reduction is carried out directly on intermediate IIa, the hydroxyl group of product IIa is protected to form intermediate IIIb before the subsequent thiazolidine ring cleavage step.

Hydroxyl protection is achieved according to known procedures using conventional hydroxy-protecting groups known to those skilled in the art. Protection of the hydroxyl functional group of intermediate IIa and IIIa is desirable to prevent side reactions and reduced yields in later steps of the reaction sequence, e.g. the ring degradation step with mercuric salt. Suitable hydroxy groups may be, for example, acyl groups such as benzyloxycarbonyl, benzhydryloxycarbonyl, trityloxycarbonyl, p-nitrobenzyloxycarbonyl and 2,2,2-trichloroethoxycarbonyl, aralkyl groups such as benzyl, benzhydryl, trityl or p-nitrobenzyl or triorganosilyl groups such as tri($C_1$–$C_6$)alkylsilyl (e.g. trimethylsilyl, triethylsilyl, triisopropylsilyl, isopropyldimethylsilyl, t-butyldimethylsilyl, methyldiisopropylsilyl or methyl-di-t-butylsilyl), triarylsilyl (e.g. triphenylsilyl, tri-p-xylylsilyl) or triaralkysilyl (e.g. tribenzylsilyl). Examples of these and other suitable hydroxy-protecting groups and methods for their formation and removal are known in the art, e.g. see *Protective Groups in Organic Synthesis*, T. W. Greene, John Wiley & Sons, New York, 1981, Chapter 2.

While any conventional hydroxyl protecting group may be utilized in the reductive removal of substituent X, it was unexpectedly found that use of a bulky triorganosilyl hydroxy protecting group such as t-butyldimethylsilyl, t-butyldiphenylsilyl or triisopropylsilyl results in essentially exclusive formation (e.g. ~95%) of the desired trans isomer IIIb, while use of other hydroxy protecting groups or unprotected intermediate IIa results in co-production of the undesired cis isomer in sufficient amounts to require a separation step. Thus, it is a preferred embodiment of the present invention that intermediate IIa be converted to the corresponding hydroxyl-protected intermediate IIb where R" is a bulky triorganosilyl group, most preferably t-butyldimethylsilyl, t-butyldiphenylsilyl or triisopropylsilyl, and then this intermediate be subjected to the reduction step so as to provide essentially stereoselective formation of the trans intermediate IIIb.

The hydroxy protecting group selected should be one that is readily removable at a later stage of the reaction process. Triorganosilyl protecting groups are advantageously used (in addition to certain of these groups, i.e. the bulky triorganosilyl groups such as triisopropylsilyl, t-butyldiphenylsilyl or t-butyldimethylsilyl being preferred for an essentially stereocontrolled reduction step) since such groups can be readily removed under mild conditions, e.g. by treatment with methanolic HCl or with fluoride ion (e.g. tetra-n-butylammonium fluoride/tetrahydrofuran), without destroying the sensitive β-lactam nucleus. Silylation may be accomplished by use of a suitable silylating agent (e.g. silylchloride or silyltriflate) in an inert organic solvent such as methylene chloride, tetrahydrofuran, dioxane, dimethoxyethane, chloroform or diethyl ether and in the presence of base, e.g. an organic base such as pyridine, 2,6-lutidine, imidazole or triethylamine. While silylation can be carried out over a wide temperature range, it is preferred to use temperatures in the range of about $-40°$ C. up to about $+5°$ C. In a preferred embodiment the hydroxy group of intermediate IIa or IIIa is silylated with triisopropylsilyltriflate, t-butyldiphenylsilyltriflate or t-butyldimethylsilyltriflate in methylene chloride, tetrahydrofuran, chloroform, toluene or diethyl ether, most preferably tetrahydrofuran or methylene chloride, at a temperature around $0°$ C.

Intermediate IIa or hydroxy-protected intermediate IIb is subjected to reduction so as to remove the halogen or phenylseleno group and produce the desired 5R, 6S product

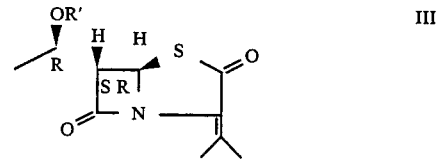 III wherein R' is hydrogen or a conventional hydroxy-protecting group; most preferably a bulky triorganosilyl group such as triisopropylsilyl, t-butyldiphenylsilyl or t-butyldimethylsilyl. Reduction may be carried out with a chemical reducing agent such as zinc-silver couple, zinc-copper couple, $SnI_2$, tin hydride, zinc amalgam, zinc or zinc activated with acid (e.g. HCl or $CH_3COOH$) or by means of catalytic hydrogenation. An inert solvent is generally employed such as tetrahydrofuran, diethyl ether, methanol, ethanol, isopropanol, acetic acid, mixtures of ether and alcoholic solvents, etc. In a preferred embodiment zinc-silver couple is used in a THF/$CH_3OH$ solvent system. Another preferred embodiment involves use of zinc activated with acid, preferably HCl or acetic acid. Reduction may be achieved over a wide temperature range, e.g. $-45°$ C. up to room temperature. Generally the reduction step provides the most desired trans (5R, 6S) isomer as the predominant product with only minor amounts of the less desired cis isomer. As mentioned above, if intermediate IIa is converted to a hydroxy-protected intermediate IIb wherein R" is a bulky triorganosilyl group such as triisopropylsilyl, t-butyldimethylsilyl or t-butyldiphenylsilyl, reduction of IIb is essentially stereospecific with the desired trans isomer being almost exclusively formed. Thus, under such preferred conditions, the product of the reduction step can be used directly in the subsequent reaction steps without the necessity of first separating out the undesired cis isomer co-product.

After reduction the anhydropenicillin intermediate III, following hydroxy group protection if required, is converted by per se known reaction steps to the desired acetoxyazetidinone intermediate I. Thus, in the most preferred embodiment, the hydroxy-protected intermediate IIIb, having the desired chirality at carbons 5, 6 and 8, is subjected to thiazolidine ring degradation, e.g. with Hg(OAc)₂ in acetic acid, to produce the intermediate

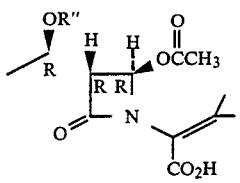    IV wherein R" is a conventional hydroxy-protecting group and this intermediate IV is then oxidized to form the desired optically active intermediate I. Thiazolidine ring degradation is described in the literature and may be accomplished, for example, by reacting intermediate IIIb in acetic acid or a mixture of acetic acid and an inert organic solvent such as tetrahydrofuran or dioxane with an mercuric salt such as Hg(OAc)₂ or HgCl₂ at a temperature between about 0° and 40° C.

Removal of the crotonate moiety is accomplished by oxidation of intermediate IV. Use of ozonolysis (e.g. O₃ in CH₃OH) allows acid IV to be directly oxidized to intermediate I. Chemical oxidizing agents such as KMnO₄, KMnO₄ with phase transfer catalysts, KMnO₄/NaIO₄ and RuO₄/NaIO₄ generally require that the carboxylic acid functional group of IV be protected prior to oxidation, e.g. by conversion to an ester or anhydride.

The above-described reaction can of course, with judicious selection of solvents, be carried out without isolation of one or more intermediates in the sequence. Alternatively, where possible, intermediates may be isolated as crystalline materials and optionally purified as by recrystallization before proceeding with subsequent reaction steps.

It will be apparent to those skilled in the art that the present process, although described in terms of producing acetoxyazetidinone I, can be readily modified to provide other useful azetidinone intermediate of the type

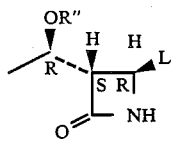

where L represents a conventional leaving group. For example, intermediate IIIb above may be subjected to chlorinolysis (Cl₂/CH₂Cl₂, −15° C.) to give

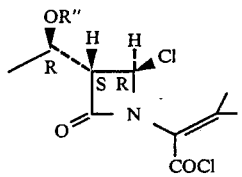

which may be oxidized, after conversion to the corresponding acid or ester, as described above for the corresponding acetoxy derivative to give the chloro intermediate

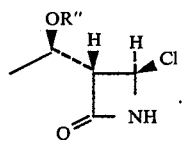

The (R)-hydroxyethyl azetidinone intermediates produced according to the present invention, i.e. intermediate I or an analog thereof such as the above-mentioned chloro compound, are readily converted by known methods to thienamycin and other carbapenem and penem derivatives having useful antibacterial activity.

The following examples illustrate but do not limit the scope of the present invention. All temperatures referred to below are in degrees Celsius unless otherwise indicated.

EXAMPLE 1

Preparation of (4R)-acetoxy-(3R)-[(1'R)-(tert-butyldimethylsilyloxy)ethyl]-2-azetidinone from anhydro-6,6-dibromopenicillin

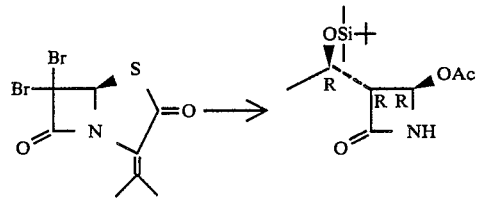

A. Anhydro-6,6-dibromopenicillin

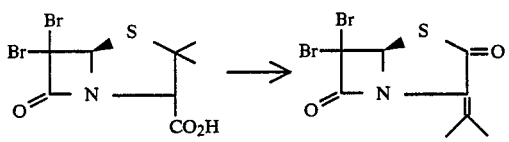

A cold (ice-methanol bath) solution of 6,6-dibromopenicillanic acid (20.00 g, 55.56 mmol) in CH₂Cl₂ (200 mL) was treated dropwise with triethylamine (58.4 mmol, 8.00 mL) and stirred for 15 min. To the solution was added dropwise trifluoroacetic anhydride (8.40 mL, 61.2 mmol). It was stirred for 30 min, then treated dropwise wih pyridine (4.8 mL, 61.2 mmol). The mixture was stirred for 30 min at −10° C. and then for 18 h at 5°. The mixture was successively washed with 1N aqueous HCl, water, 1M aqueous NaHCO₃ and brine and dried (MgSO₄). The residue obtained upon solvent evaporation was redissolved in ethyl acetate (EtOAc), and treated with activated charcoal to give title compound: mp 102°–103° C. (CH$_3$OH), (16.1 g, 47.2 mmol, yield 85%): $^1$Hmr (CDCl$_3$, 80 MHz) δ: 5.80 (1H, s, H-5), 2.21 (3H, s, CH$_3$), and 2.15 ppm (3H, s, CH$_3$); ir (CH$_2$Cl$_2$) ν$_{max}$: 1800 (s, β-lactam C=O), 1708 (s, lactone C=O) and 1640 cm$^{-1}$ (w, olefin); [α]$_D^{22}$+88.9° (c 0.144, CH$_3$OH); Anal. calcd. for C$_8$H$_7$NO$_2$SBr$_2$: C 28.17, H 2.07, N 4.10; found C 28.08, H 1.98, N 4.06.

B.
Anhydro-6α-bromo-6β-[(1'R)-hydroxyethyl]penicillin

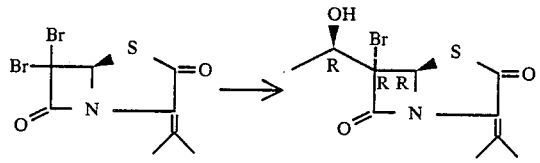

Anhydro-6,6-dibromopenicillin (15.02 g, 44 mmol) was dissolved in cold (−78°) THF (450 mL), treated dropwise with a 2.85M solution of MeMgBr (18.0 mL, 51.3 mmol) in ether and stirred for 20 min at −78° C. The resulting magnesium enolate was trapped with excess acetaldehyde (25 mL, 0.45 mol) and stirred for 20 min. The cooling bath was removed and to the reaction mixture was added 1N aqueous HCl (70 mL) and ether (300 mL). The aqueous phase was removed and extracted with ether (2×200 mL). The organic phases were combined, washed successively with 1N aqueous HCl, water, 1M aqueous NaHCO$_3$ and brine and dried (MgSO$_4$). The solvent was removed to give title compound (13.08 g; 42.7 mmol; yield 97%) as an oil: $^1$Hmr (CDCl$_3$) δ: 5.61 (1H, s, H-5), 4.28 (1H, q, J=6.0, H-1'), 2.21 (3H, s, CH$_3$) 2.16 (3H, s, CH$_3$), 1.64 (1H, bs, OH), and 1.31 ppm (3H, d, J=6.0 Hz, CH$_3$); ir (CH$_2$Cl$_2$) ν$_{max}$: 3560 (m, OH), 1785 (s, β-lactam C=O), 1710 (s, lactone C=O) and 1635 cm$^{-1}$ (m, olefin); [α]$_D^{22}$+83.8° (c 0.128, MeOH); Anal. calcd. for C$_{10}$H$_{12}$NO$_3$SBr: C 39.23, H 3.95, N 4.57; found C 38.31, H 4.63, N 4.61.

C.
Anhydro-6α-bromo-6β-[(1'R)-(tert-butyldimethylsilyloxy)ethyl]penicillin

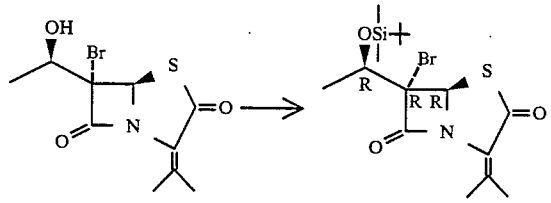

To a cold (ice bath) methylene chloride (60 mL) solution of anhydro-6α-bromo-6β-[1'R)-hydroxyethyl]-penicillin (6.0 g, 19.6 mmol) was added first 2,6-lutidine (4.50 mL, 39 mmol) followed by the dropwise addition of tert-butyldimethylsilyl triflate (7.8 mL, 34 mmol). The mixture was stirred (5° C.) for 1 h, then washed with 1N aqueous HCl, water, 1M aqueous NaHCO$_3$ and brine. The resulting organic phase was dried (MgSO$_4$), diluted with an equal volume of a mixture of ether-petroleum ether (1:2) and treated with activated charcoal. The solid residue upon solvent evaporation was redissolved in hot hexane and allowed to crystallize to give title compound, 5.35 g. The mother liquor was concentrated, treated with activated charcoal and allowed to crystallize in the cold (5° C, 1.28 g). Combination of the two crops gave the protected hydroxyl derivative (6.63 g, 15.7 mmol, yield 80.6%) mp 116°–117° C. (MeOH): $^1$Hmr (CDCl$_3$) δ: 5.53 (1H, s, H-5), 4.27 (1H, q, J=6.1 Hz, H-1'), 2.20 (3H, s, CH$_3$), 2.13 (3H, s, CH$_3$) 1.28 (3H, d, J=6.1 Hz, CH$_3$), 0.91 (9H, s, tert-butyl), 0.09 (3H, s, CH$_3$) and 0.07 (3H, s, CH$_3$); ir (CH$_2$Cl$_2$) ν$_{max}$: 1785 (s, β-lactam C=O), 1700 (s, lactone C=O) and 1635 cm$^{-1}$ (m, olefin); [α]$_D^{22}$+119.6° (c 0.14 MeOH); Anal. calcd. for C$_{16}$H$_{27}$NO$_3$SBrSi: C 45.60, H 6.45, N 3.32; found: C 46.38, H 6.02, N 3.23.

D.
Anhydro-6α-[(1'R)-(tert-butyldimethylsilyoxy)ethyl]-penicillin

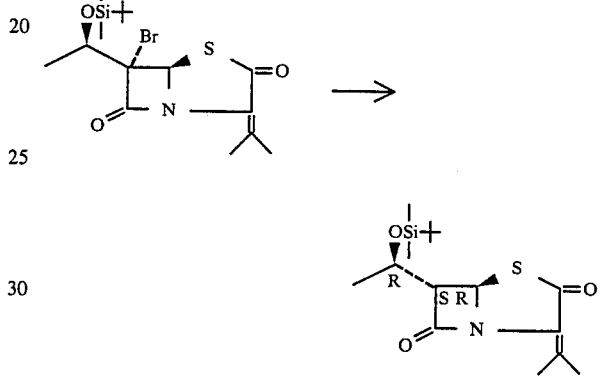

To a solution of anhydro-6α-bromo-6β-[(1'R)-(tert-butyldimethylsilyloxy)ethyl]penicillin (1.00 g, 2.38 mmol) in a 25% mixture of THF-MeOH (25 mL) cooled at −45° C. was added Zn (Ag)* (10 g). The mixture was stirred until all the starting material was consumed (TLC plate, Rf 0.4, 2% CH$_3$CN/CH$_2$Cl$_2$ and then filtered through CELITE pad into a cold 1M aqueous NH$_4$Cl solution. The phases were shaken, separated and the aqueous phase was extracted with ether (3×10 mL). The organic phases were combined and successively washed with 1N aqueous HCl, water, 1M aqueous NaHCO$_3$, brine and dried (MgSO$_4$). Evaporation of the solvent afforded an oil that crystallized under vacuum (815 mg, 2.38 mmol, yield 99.6%). HPLC analysis of the solid showed the following ratio: Starting material 0.70%, the cis isomer 2.51% and title compound 96.79%, mp 56°–7° C. (MeOH); $^1$Hmr (CDCl$_3$) δ: 5.29 (1H, d, J=1.8, H-5), 4.34 (1H, dq, J=6.3, J=3.5 Hz, H-1'), 3.52 (1H, dd, J=3.5 Hz, J=1.8 Hz, H-6), 2.17 (3H, s, CH$_3$), 2.08 (3H, s, CH$_3$), 1.25 (3H, d, J=6.3 Hz, CH$_3$), 0.89 (9H, s, tert-butyl), and 0.09 ppm (6H, s, CH$_3$); ir (CH$_2$Cl$_2$) ν$_{max}$: 1775 (s, β-lactam C=O), 1695 (s, lactone C=O) and 1635 cm$^{-1}$ (m, olefin); [α]$_D^{22}$+42.8° (c 0.114, MeOH); Anal. calcd. for C$_{16}$H$_{27}$NO$_3$SSi: C 56.10, H 8.24, N 4.09, S 9.38; found: C 56.65, H 7.82, N 4.07, S 9.04. The corresponding 6-β-(1'R) isomer was isolated as an oil: $^1$Hmr (CDCl$_3$) δ: 5.35 (1H, d, J=4.6, H-5), 4.31 (1H, dq, J=6.0, J=9.4, H-1'), 3.83 (1H, dd, J=4.6, J=9.4, H-6), 2.18 (3H, s, CH$_3$), 2.08 (3H, s, CH$_3$), 1.23 (3H, d, J=6.0, CH$_3$), 0.89 (9H, s, tert-butyl), 0.10 (3H, s, CH$_3$) and 0.06 ppm (3H, s, CH$_3$); ir (CH$_2$Cl$_2$) δ$_{max}$: 1785 (s, β-lactam C=O), 1695 (s, lactone C=O), and 1635 cm$^{-1}$ (m, olefin); [α]$_D^{22}$+171.2° (c 0.084, MeOH).

* Zinc silver couple was prepared from one part of silver acetate and 11.7 parts of Zn.

E.
α-[(3R)-[(1'R)-(tert-butyldimethylsilyloxy)ethyl]-(4R)-acetoxy-2-azetidinon-1-yl]-β-methylcrotonic acid

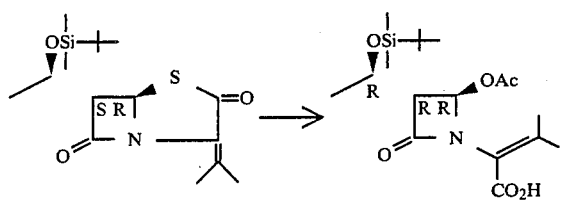

A solution of anhydro-6α-[(1'R)-(tert-butyldimethylsilyloxy)ethyl]penicillin (5.00 g, 14.6 mmol) in acetic acid (75 mL) was treated at 22° C. with mercuric acetate (14 g, 44 mmol) and stirred for 24 h. To the mixture was added additional mercuric acetate (9.3 g, 29 mmol) and the stirring was continued for 24 more hours. The reaction mixture was filtered through a CELITE pad and the solid was washed with acetic acid. The filtrate was diluted with water (150 mL) and extracted with ether (5×40 mL). The organic extracts were combined, washed with water (3×40 mL) brine, dried (MgSO$_4$) and treated with charcoal. Solvent evaporation gave an oil which crystallized under vacuum (5.33 g, 13.8 mmol, yield 95%), mp 119°-20° C. (CH$_2$Cl$_2$/pet. ether, 9/1); $^1$Hmr (CDCl$_3$) δ: 6.32 (1H, d, J=1.4, H-4), 4.24 (1H, center of 5 lines, J=6.0, H-1'), 3.20 (1H, dd, J=1.4, J=5.8, H-3), 2.24 (3H, s, CH$_3$), 2.05 (3H, s, CH$_3$CO$_2$), 1.97 (3H, s, CH$_3$), 1.29 (3H, d, J=6.3, CH$_3$), 0.86 (9H, s, tert-butyl), 0.08 (3H, s, CH$_3$), and 0.05 ppm (3H, s, CH$_3$); ir (CH$_2$Cl$_2$) $v_{max}$: 1770 (s, β-lactam C=O), 1745 (m, CH$_3$C=O), 1690 (m, CO$_2$H), and 1620 cm$^{-1}$ (w, olefin); [α]$_D^{22}$+18.9° (c 0.088, MeOH); Anal. calcd. for C$_{18}$H$_{31}$NO$_6$Si: C 56.07, H 8.10, N 3.63; found: C 56.00, H 8.25, N 3.73.

F.
(4R)-Acetoxy-(3R)-[(1'R)-(tert-butyldimethylsilyloxy)ethyl]-2-azetidinone

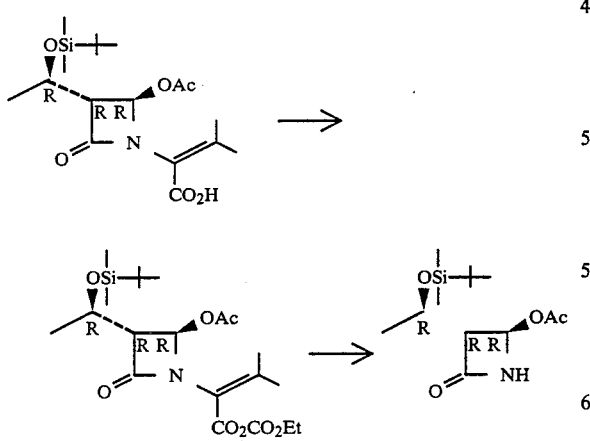

To a solution of α-(3R)-[(1'R)-(tert-butyldimethylsilyloxy)ethyl]-(4R)-acetoxy-2-azetidinon-1-yl]-β-methyl crotonic acid (2.0 g, 5.2 mmol) in CH$_2$Cl$_2$ (30 mL) was added at −15° C. (ice-MeOH bath) EEDQ (1.63 g, 6.20 mmol). The cooling bath was removed and the reaction mixture was stirred for 18 h at 22° C. It was successively washed with 1N aqueous HCl, water, 1M aqueous NaHCO$_3$, brine and dried (MgSO$_4$). Evaporation of the solvent afforded a mixed anhydride (2.14 g, yield 93.3%) as a carboxylic acid-protected derivative; $^1$Hmr (CDCl$_3$) δ: 6.23 (1H, d, J=1.4, H-4), 4.32 (2H, q, J=7.1, CH$_2$CH$_3$), 4.05-4.39 (1H, m, J=6.1, H-1'), 3.23 (1H, dd, J=1.4, J=6.1, H-3), 2.25 (3H, s, CH$_3$), 2.06 (3H, s, CH$_3$CO), 1.17 (3H, s, CH$_3$), 1.35 (3H, t, J=7.1, CH$_3$CH$_2$), 1.29 (3H, d, J=6.1, CH$_3$), 0.86 (9H, s, tert-butyl), 0.08 (3H, s, CH$_3$) and 0.05 ppm (3H, s, CH$_3$); ir (CH$_2$Cl$_2$) $v_{max}$: 1800 (s, mixed anhydride), 1775 (s, β-lactam C=O), 1750 (s, Acetate C=O) and 1625 cm$^{-1}$ (w, olefin).

The mixed anhydride (2.10 g, 4.76 mmol) so obtained was dissolved in CH$_2$Cl$_2$ (30 mL) cooled to −78° C. (acetone-dry ice bath) and ozonolyzed until all starting material disappeared (1.5 h). The cold (−78° C.) solution of ozonide was reduced with (CH$_3$)$_2$S (6 mL) was stirred at room temperature for 1.5 h. Methanol (30 mL) was added followed by 2,6-lutidine (1.2 mL). The mixture was stirred at 22° C. for 2 h, diluted with ether, washed with 1N aqueous HCl, water, 1M aqueous NaHCO$_3$, brine and dried (MgSO$_4$). Evaporation of the solvent gave title compound (1.31 g, 4.56 mmol, yield 95%) as a white solid; mp 104°-106° C. ether/pet. ether: 1/1 [literature* mp 104°-106° C.]; [α]$_D^{22}$+47.4° (c 0.136, CHCl$_3$). [literature* [α]$_D$+48.8° (c 0.41, CHCl$_3$)].

*Chem. Pharm. Bull (tokyo) 29 2899 (1981).

EXAMPLE 2
6α-Bromo-6β-[(1'R)-hydroxyethyl]anhyropenicillin and
6α-bromo-6β-[(1'R)-t-butyldimethylsilyloxy)ethyl]anhydropenicillin-illustrates aldol condensation reaction at relatively high (−20° C.)temperature

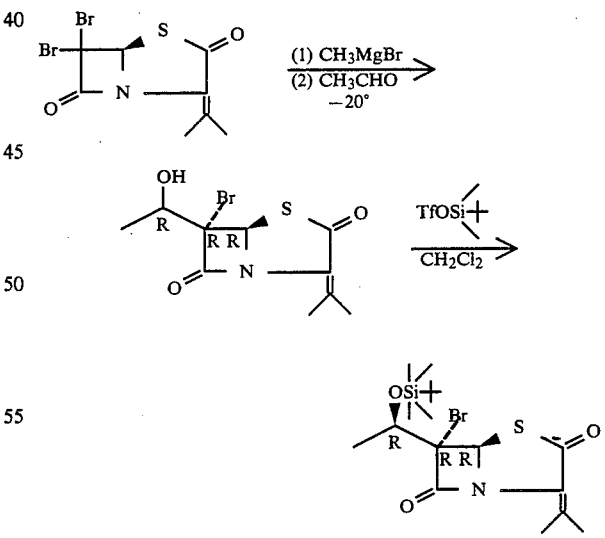

REAGENTS

| | |
|---|---|
| anhydropenicillin | 10.23 g (0.03 mole) |
| CH$_3$MgBr | 12.21 mL (0.0348 mole, 16% excess, 2.85 M solution in ether, Aldrich) |
| CH$_3$CHO | 6.6 g = 8.4 mL (0.15 mole, d. 0.788, Aldrich) |
| THF | 150 mL (dried over molecular sieves) |

-continued

| 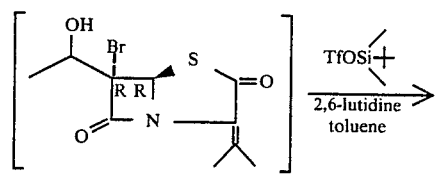 | 11.54 g ≡ 10.02 mL (0.0436 mole, d. 1.151 distd) |
|---|---|
| 2,6-lutidine | 6.42 g ≡ 6.98 mL (0.06 mole, d. 0.92, Aldrich) |
| CH₂Cl₂ | 100 mL (dried over molecular sieves) |

PROCEDURE

To a solution of anhydro-6,6-dibromopenicillin (10.23 g) in dry THF (150 mL) cooled to −20°, there was added dropwise methylmagnesium bromide (12.21 mL) over 10 min. while maintaining the temperature at −15°−−20°. The resulting solution was stirred at −20 for 10 min., and then acetaldehyde (8.4 mL) was, initially dropwise, added over 5 min., maintaining the temperature at −15°−−20°. The solution was stirred at −20° for 15 min. To the reaction mixture was added saturated ammonium chloride (10 mL) followed by water (80 mL). The mixture was then extracted with ethyl acetate (150 mL, 50 mL). The ethyl acetate extract was washed with brine (twice, 100 mL each), dried over anhydrous sodium sulfate and concentrated to give an oil (8.9 g, 97%). HPLC* 92% of cis, no trans isomer, 8% of impurities.

| *Column: | μ Porasil (Waters) |
|---|---|
| Solvent: | 3% CH₃CN/CH₂Cl₂ |
| Flow: | 90 mL/h |
| Detection: | uv 275 nm |
| Attenuation: | 0.2 |

The above crude oil was dissolved in dry CH₂Cl₂ (100 mL) cooled to 0°. There was added 2,6-lutidine (6.98 mL) followed by dropwise addition of t-butyldimethylsilyl trifluoromethylsulfonate (10.02 mL) over 20 min., maintaining the temperature at 0°–5°. The resulting solution was stirred at 0°–5° for 1 hour. TLC (silica, ether-pet. ether 1:1, I₂ showed completion of reaction. The reaction mixture was washed with 1N HCl (100 mL), saturated NaHCO₃ (100 mL) and brine (100 mL) respectively, dried over anhydrous Na₂SO₄ and concentrated to give a dark oil that gradually solidified. This oil was dissolved in warm pet. ether, carbon-treated and concentrated to dryness (14 g). This crude solid was redissolved in warm isopropanol (70 mL), diluted with water (35 mL) while the solution was warm, cooled to 0° and filtered. The cake was washed with isopropanol/H₂O 2:1 and dried in a vacuum desiccator. Yield 7.0 g (55.5% over 2 steps).

EXAMPLE 3

6α-Bromo-6β-[(1'R)-(t-butyldimethylsilyloxy)ethyl]anhydropenicillin-illustrates use of CH₃MgCl as Grignard reactant

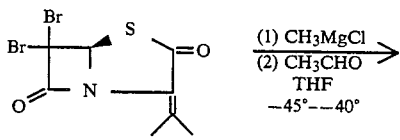

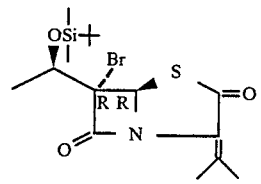

REAGENTS

| anhydropenicillin | 34.1 g (0.1 mole) |
|---|---|
| CH₃MgCl | 39.6 mL (0.116 mole, 16% excess, 2.9 M solution in THF) |
| CH₃CHO | 28 mL ≡ 22 g (0.5 mole, d.0.788) |
| THF | 350 mL (dried over molecular sieves) |
| 2,6-lutidine | 23.3 mL ≡ 21.4 g (0.2 mole, d.0.92, dried over KOH) |
| TfOSi—⧫ | 32 g ≡ 27.6 mL (0.12 mole, d.1.151) |
| toluene | 800 mL |

PROCEDURE

A solution of anhydro-6,6-dibromopenicillin (34.1 g) in dry THF (350 mL) was cooled to −45° and there was added dropwise methylmagnesium chloride (39.6 mL) over 20 min., maintaining the temperature below −40°. The resulting solution was stirred at −45°−−40° for 10 min. and acetaldehyde (28 mL) was, initially dropwise, added over 5 min. while maintaining the temperature below −30°. The solution was stirred at −40° for 15 min. To the reaction mixture was added saturated ammonium chloride (35 mL), followed by addition of water (400 mL). The mixture was extracted with toluene (350 mL and 150 mL). The toluene extract was washed with brine (2×300 mL), dried over anhydrous magnesium sulfate and concentrated until the volume became ~100 mL. To the concentrated solution was added toluene (300 mL) followed by continued concentration to ~300 mL¹.

The toluene solution was cooled to 0° and there was added 2,6-lutidine (23.3 mL) followed by dropwise addition of triflate (27.6 mL) over 15 min. while maintaining the temperature at 0°–5°. The resulting solution was stirred at 0° for 1 h.². To the reaction mixture was added water (250 mL) and the pH was adjusted to 2.5 from 5.0 with conc. hydrochloric acid (~8 mL).

The organic layer was separated. To the organic layer was added water (250 mL) and the pH was adjusted to 8.0 with 1% sodium hydroxide (~10 mL). The organic layer was washed with brine (2×250 mL), carbon-treated (15 g) and concentrated to ~50 mL. To the concentrate were added isopropanol (200 mL) and water (dropwise) (100 mL) under stirring. 100 mL of solvent was removed under reduced pressure to give a slurry that was cooled to 0°, stirred for 0.5 h and filtered. The cake was washed with ice-cold isopropanol-water 2:1 (80 mL) and dried in a vacuum desiccator. Yield 29.0 g (69%) mp 95°-100°. The crude product was recrystallized as follows: dissolved in toluene (150 mL), carbon-treated, concentrated as much as possible, isopropanol (200 mL) added, followed by dropwise addition of water (100 mL) under ice-cooling and stirring. The precipitated product was filtered off, washed with ice-cold isopropanol-water 2:1 and dried in a vacuum desiccator. Yield 21.0 g (50%); mp 104°-108°.

| *Column: | Porasil (Waters) |
|---|---|
| Solvent: | 3% $CH_3CN/CH_2Cl_2$ |
| Flow: | 90 mL/h |
| Detection: | uv 275 nm |
| Attenuation: | 0.2 |

[1]HPLC* showed 92% purity, no trans isomer.
[2]TLC: silica gel, ether-pet. ether 1:1, $I_2$

EXAMPLE 4

6α-[(1'R)-(t-butyldimethylsilyloxy)ethyl]anhydropenicillin-illustrates use of zinc/acetic acid reduction

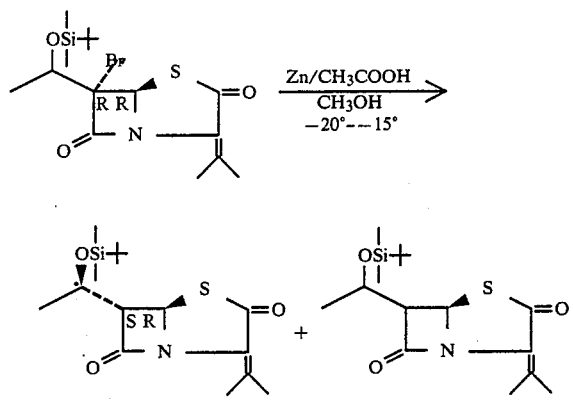

REAGENTS

| anhydropenicillin | 42.0 g (0.1 mole) |
|---|---|
| zinc dust | 42.0 g (0.65 mole, Anachemia) |
| acetic acid | 11 mL = 11.54 g (0.19 mole, d 1.049, glacial) |
| $CH_3OH$ | 1000 mL |

PROCEDURE

In a 2 L 3-necked flask fitted with a mechanical stirrer, a thermometer, a dropping funnel and nitrogen inlet and outlet tubes was suspended anhydro-6α-bromo-6β-[(1'R)-hydroxyethyl]penicillin (42 g) in methanol (100 mL). The reaction mixture was cooled to −20° and there was added zinc dust (42 g) followed by slow addition of acetic acid (11 mL). The resulting mixture was stirred at −25°-−15° for 0.5 h. TLC (silica, ether-pet. ether 1:3, $I_2$ or molybdate solution) showed completion of reaction. The reaction mixture was filtered on CELITE into saturated ammonium chloride (100 mL) and the CELITE was washed with methylene chloride. The filtrate was diluted with water (500 mL) and extracted with methylene chloride (1000 mL and 500 mL). The methylene chloride extract was washed with brine (1000 mL), dried over anhydrous magnesium sulfate and concentrated to give an oil (34 g, 100% crude) that gradually crystallized. Analysis showed trans 83.3%, cis 5.7%, impurities: 11%.

EXAMPLE 5

Preparation of Anhydro 6α- and 6β-[(1'R)-hydroxyethyl]penicillin

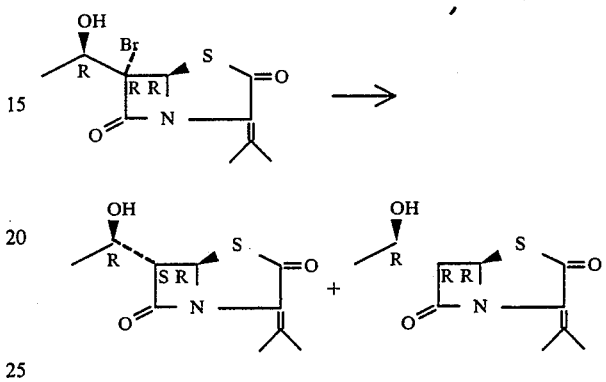

A cold (ice-methanol bath) solution of anhydro-6α-bromo-6β-[(1'R)-hydroxyethyl]penicillin (4.20 g, 13.7 mmol) in methanol (40 mL) was treated with Zn(Ag) (4.2 g) and stirred for 15 min. More Zn(Ag) (1.1 g) was added and the mixture was stirred for 10 min. The cold suspension was filtered through a CELITE pad into cold concentrated aqueous $NH_4Cl$. The solid was washed with ether and the two phases were separated. The aqueous phase was extracted with ether (2×20 mL). The ether extracts were combined and successively washed with 1N aqueous HCl, water, 1M aqueous $NaHCO_3$ and brine and then dried. The residue upon solvent evaporation was triturated with a cold mixture of petroleum ether/ether: 9/1 to give the 6α-isomer (1.3 g, 5.7 mmol, yield 42%)* as a white solid: mp 173°-4° C. ($CH_2Cl_2$/ether: 2/8); [1]Hmr ($CDCl_3$) δ: 5.28 (1H, d, J=1.7, H-5), 4.35 (1H, quintet, J=6.2, H-1'), 3.57 (1H, dd, J=6.2, J=1.7, H-6), 2.19 (3H, s, $CH_3$), 2.11 (3H, s, $CH_3$), 1.72 (1H, bs, OH) and 1.40 ppm (3H, d, J=6.3, $CH_3$); ir ($CH_2Cl_2$) $v_{max}$: 3500 (w, OH), 1775 (s, β-lactam C=O), 1695 (s, lactone C=O) and 1635 cm$^{-1}$ (m, olefin); Anal. calcd. for $C_{10}H_{13}NO_3S$; C 52.84, H 5.76, N 6.16; found: C 52.86, H 5.72, N 6.08.

*Reaction conditions not optimized; when repeated at −50° C. it gave a 56.6% yield of the 6α-isomer The cold ether/petroleum ether: 1/9 mixture was evaporated and the pure 6β-isomer separated on preparative TLC (2% $CH_3CN/CH_2Cl_2$); [1]Hmr ($CDCl_3$) δ: 5.40 (1H, d, J=4.6, H-5), 4.36 (1H, dq, J=6.1, J=9.0, H-1'), 3.74 (1H, dd, J=9.0, J=4.6, H-6), 2.19 (3H, s, $CH_3$), 2.25-1.90 (1H, bs, OH), 2.09 (3H, s, $CH_3$) and 1.27 ppm (3H, d, J=6.0, $CH_3$); ir ($CH_2Cl_2$) $v_{max}$: 3580 (w, OH), 1770 (s, β-lactam C=O), 1700 (s, lactone C=O) and 1640 cm$^{-1}$ (m, olefin).

We claim:

1. A process for the preparation of an intermediate of the formula

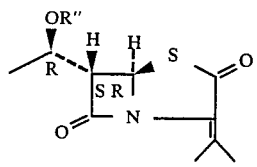    IIIb wherein R″ is a conventional hydroxy-protecting group selected from triisopropylsilyl, t-butyldimethylsilyl or t-butyldiphenylsilyl, which comprises the steps of
(a) reacting a 6,6-disubstituted anhydropenicillin of the formula

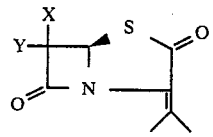    V wherein X and Y are each independently chloro, bromo, iodo or phenylseleno with a reagent selected from a Grignard reagent of the formula $R_1MgX$ or an organolithium compound of the formula $R_1Li$ in which $R_1$ is (lower alkyl or $C_6$–$C_{10}$ aryl and X is as defined above in an anhydrous inert organic solvent and at a temperature in the range of about 0° to −78° C. and subsequently adding acetaldehyde to exclusively produce the cis isomer of the formula

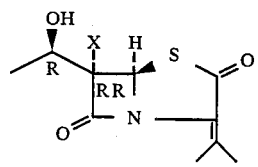    IIa wherein X is as defined above:
(b) converting intermediate IIa to the corresponding intermediate of the formula

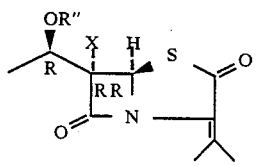    IIb wherein R″ and X are as defined above; and
(c) subjecting intermediate IIb to reduction in an inert solvent and isolating the so-produced 5,6-trans isomer of the formula

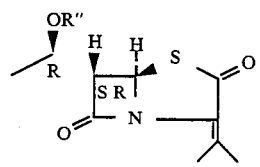    IIIb wherein R″ is as defined above.
2. A process for the preparation of an intermediate of the formula

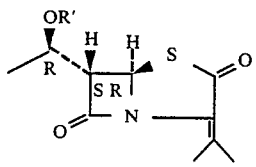    III wherein R′ is hydrogen or a conventional hydroxy-protecting group selected from triisopropylsilyl, t-butyldimethylsilyl or t-butyldiphenylsilyl, which comprises the steps of
(a) reacting a 6,6-disubstituted anhydropenicillin of the formula

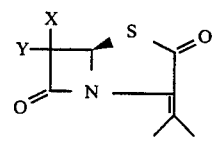    V wherein X and Y are each independently chloro, bromo, iodo or phenylseleno with a reagent selected from a Grignard reagent of the formula $R_1MgX$ or an organolithium compound of the formula $R_1Li$ in which $R_1$ is (lower alkyl or $C_6$–$C_{10}$ aryl and X is as defined above in an anhydrous inert organic solvent and at a temperature in the range of about 0° to −78° C. and subsequently adding acetaldehyde to exclusively produce the cis isomer of the formula

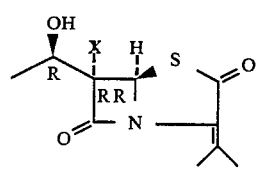    IIa wherein X is as defined above;
(b) subjecting intermediate IIa to reduction in an inert solvent and isolating the so-produced 5,6-trans isomer of the formula

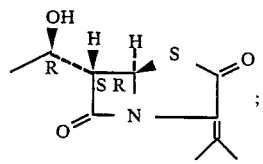    IIIa and, if desired,
(c) converting intermediate IIIa to the corresponding intermediate of the formula

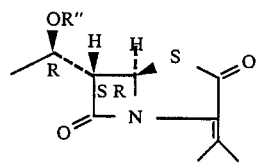    IIIb wherein R″ is as defined above.
3. A process for the preparation of a compound of the formula

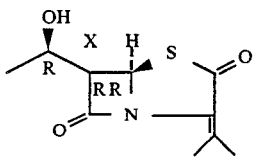

wherein X is chloro, bromo, iodo or phenylseleno which comprises reacting an intermediate of the formula

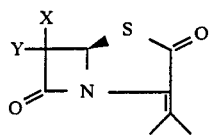

wherein X and Y are each independently chloro, bromo, iodo or phenylseleno with a reagent selected from a Grignard reagent of the formula $R_1MgX$ or an organolithium compound of the formula $R_1Li$ in which $R_1$ is (lower) alkyl or $C_6$–$C_{10}$ aryl and X is as defined above in an anhydrous inert organic solvent and at a temperature in the range of about 0° to −78° C. and subsequently adding acetaldehyde to exclusively produce the desired (8R)-hydroxyethyl cis isomer of formula II.

4. The process of claim 3 wherein the starting material is

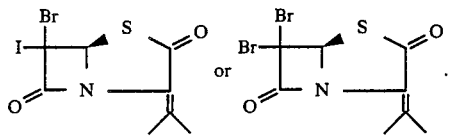

5. The process of claim 3 wherein the starting material is 6,6-dibromoanhydropenicillin.

6. The process of claim 3, 4 or 5 wherein the Grignard reagent $CH_3MgBr$ is used.

7. The process of claim 3, 4 or 5 wherein the Grignard reagent $CH_3MgCl$ is used.

8. The process of claim 3 wherein 6,6-dibromoanhydropenicillin is reacted in an inert organic solvent with about a molar equivalent of methylmagnesium chloride at a temperature in the range of about −45° C. to −40° C. followed by addition of a molar excess of acetaldehyde.

9. The process of claim 3 wherein 6,6-dibromoanhydropenicillin is reacted in an inert organic solvent with about a molar equivalent of methylmagnesium bromide at a temperature of about −20° C. followed by addition of a molar excess of acetaldehyde.

10. A process for preparing a compound having the formula

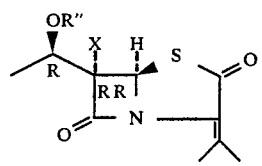

wherein X is chloro, bromo, iodo or phenylseleno and R″ is triisopropylsilyl, t-butyldimethylsilyl or t-butyldiphenylsilyl, which comprises converting the intermediate of the formula

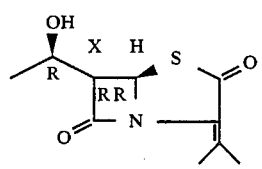

wherein X is as defined above into the corresponding intermediate wherein the hydroxyl group is protected by a triisopropylsilyl, t-butyldimethylsilyl or t-butyldiphenylsilyl hydroxyl-protecting group.

11. The process of claim 10 wherein the reaction is carried out with t-butyldimethylsilyltriflate, t-butyldiphenylsilyltriflate or triisopropylsilyltriflate in a t-butyldiphenylsilyltriflate or triisopropylsilyltriflate in a solvent selected from methylene chloride, tetrahydrofuran, chloroform, toluene or diethyl ether and in the presence of an organic base.

* * * * *